United States Patent [19]

Rinehart, Jr. et al.

[11] Patent Number: 4,762,949
[45] Date of Patent: Aug. 9, 1988

[54] ACYL AND CARBAMIMIDOYL ALKANEDIAMINES

[75] Inventors: Kenneth L. Rinehart, Jr., Urbana, Ill.; Guy T. Carter, Suffern, N.Y.; Michael T. Cheng, Urbana, Ill.

[73] Assignee: University of Illinois Foundation, Urbana, Ill.

[21] Appl. No.: 460,287

[22] Filed: Jan. 24, 1983

Related U.S. Application Data

[63] Continuation of Ser. No. 50,139, Jun. 20, 1979, abandoned.

[51] Int. Cl.$^4$ ............... C07C 103/22; C07C 103/127; C07C 103/133
[52] U.S. Cl. ................... 564/183; 544/322; 564/51; 564/57; 564/59; 564/123; 564/189; 564/190; 564/204; 564/215; 564/217
[58] Field of Search ............... 564/189, 123, 183, 190, 564/215, 217

[56] References Cited

PUBLICATIONS

Barker, et al., "Chemical Abstracts", vol. 95, 1981, col. 95: 6059j.
Abramson, et al., "Chemical Abstracts", vol. 71, 1969, col. 71: 37240v.
Veckenstedt, et al., "Chemical Abstracts", vol. 82, 1974, col. 82: 11147x.
Carter, et al., "J.A.C.S.", vol. 100, 1978, pp. 4302–4304.
Cheng, et al., "J.A.C.S.", vol. 100, 1978, pp. 7409–7411.

Primary Examiner—Glennon H. Hollrah
Assistant Examiner—James H. Turnipseed
Attorney, Agent, or Firm—Marshall, O'Toole, Gerstein, Murray & Bicknell

[57] ABSTRACT

Synthetically produced substantially pure biologically active compounds having the general formula

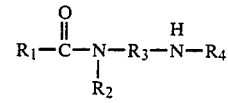

wherein
$R_1$ is $C_1$–$C_{20}$ alkyl, alkenyl, aryl, aralkyl, cycloalkyl, alkylcycloalkyl, cycloalkylalkyl, cycloalkenyl, alkylcycloalkenyl, or cycloalkenylalkyl;
$R_2$ is hydrogen, $C_1$–$C_{10}$ alkyl or an amide-substituted alkyl having up to 10 carbon atoms;
$R_3$ is a cyclic, straight or branched chain hydrocarbon group having 2–12 carbon atoms, particularly —$(CH_2)_n$—, wherein n is 2–12; or
$R_2$ and $R_3$ are linked together to form an alkylene chain; and
$R_4$ is selected from

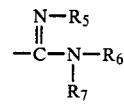

(substituted or unsubstituted carbamimidoyl),

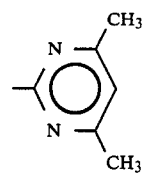

(dimethylpyrimidyl), or

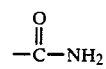

(carbamyl)

wherein each of $R_5$, $R_6$, and $R_7$ is hydrogen or the same or different $C_1$–$C_8$ alkyl group. The compounds are useful as bactericides for a wide variety of bacteria, including *S. pyogenes, B. subtilis, K. pneumoniae, M. avium, B. fragilis, C. perfringens* and *C. albicans*.

4 Claims, No Drawings

ACYL AND CARBAMIMIDOYL ALKANEDIAMINES

This is a continuation of application Ser. No. 50,139, filed June 20, 1979, now abandoned.

This invention relates to novel chemical compounds and processes for producing the same. More particularly, the invention is concerned with novel acyl and carbamimidoyl alkanediamines and derivatives thereof, having bactericidal properties.

BACKGROUND OF THE INVENTION

We have previously reported (J.A.C.S. 100, 7409 and J.A.C.S. 100, 4302) the discovery that certain marine animals, i.e., a tunicate, *Polyandrocarpa* sp., and a sponge, *Acarnus erithacus* (de Laubenfels), and their extracts possessed bactericidal, cytotoxic and other biological activities.

In accordance with the present invention, there are provided the synthetically produced substantially pure active materials described in the cited references and, in addition, other related compounds, all of which are biologically active.

SUMMARY OF THE INVENTION

The compounds of the invention have the general formula

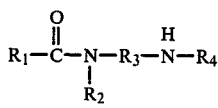

wherein $R_1$ is $C_1$–$C_{20}$ alkyl, alkenyl, aryl, aralkyl, cycloalkyl, alkylcycloalkyl, cycloalkylalkyl, cycloalkenyl, alkylcycloalkenyl, or cycloalkenylalkyl;

$R_2$ is hydrogen, $C_1$–$C_{10}$ alkyl or an amide-substituted alkyl having up to 10 carbon atoms;

$R_3$ is a cyclic, straight or branched chain hydrocarbon group having 2-12 carbon atoms, particularly —$(CH_2)_n$—, wherein n is 2-12; or $R_2$ and $R_3$ are linked together to form an alkylene chain; and $R_4$ is selected from

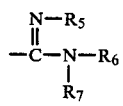

(substituted or unsubstituted carbamimidoyl),

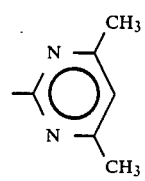

(dimethyl pyrimidyl), or

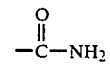

(carbamyl)

wherein each of $R_5$, $R_6$, and $R_7$ is hydrogen or the same or different $C_1$–$C_8$ alkyl group.

As used herein, the term "alkyl" means saturated, monovalent aliphatic radicals, including straight and branched chain radicals, having 1 to 20 carbon atoms, and preferably 11 to 17 carbon atoms, as illustrated by, but not limited to, methyl; n-amyl; n-hexyl; 2-heptyl; n-heptyl; 3-methyl; 2-octyl; n-octyl; 2-tetradecyl; n-hexadecyl; 2-eicosanyl, and the like.

As used herein, the term "cycloalkyl" means cyclic, saturated aliphatic radicals having 3 to 20 carbon atoms and preferably 11–17 carbon atoms, as illustrated by, but not limited to, cyclopropyl, cyclobutyl, cyclohexyl, cyclooctyl and the like.

As used herein, the terms "alkylcycloalkyl" and "cycloalkylalkyl" mean respectively a cycloalkyl group which is substituted with an alkyl group and an alkyl group which is substituted with a cycloalkyl group, as previously defined, the total of the carbon atoms in the alkylcycloalkyl group or the cycloalkylalkyl being 4 to 20 and preferably 11 to 17. Examples of said groups are octylcyclopropyl, 2-methylcyclobutyl, 4-ethylcyclohexyl, cyclopropylethyl, 2-cyclobutyl-n-octyl and the like.

The term "alkenyl" refers to straight or branched chain $C_2$–$C_{20}$ alkyl radicals from which a hydrogen atom has been removed from each of one or more pairs of adjacent carbon atoms to produce ethylenic unsaturation, such as vinyl, allyl, methallyl, 1-pentenyl, 4-undecenyl and 3,7,10- tridecatrienyl.

The terms "cycloalkenyl", "alkylcycloalkenyl", and "cycloalkenylalkyl" refer to cycloalkyl, alkylcycloalkyl and cyloalkylalkyl groups in which the cyclic structure is ethylenically unsaturated.

The term "aralkyl" refers to an aryl group, which can be a single ring, such as phenyl, or a plurality of unsaturated rings which can be bonded or fused together, such as naphthyl, substituted with an alkyl group, as previously defined.

Specific compounds which come within the scope of the invention include the following:

1-(tetradecanamidomethyl)-4-(guanidinomethyl)cyclohexane
1-(tetradecanoyl)-4-(4-guanidinomethyl)piperidine
1-benzamido-5-guanidinopentane
1-(5-phenylpentanamido)-5-guanidinopentane
1-(N-methyltetradecanamido)-5-guanidinopentane
1-[N-(7-methyloctyl)tetradecanamido]-5-guanidinopentane.

In general, the compounds of the invention can be made by a process involving successive reactions of a suitable alkane or polymethylene diamine ($NH_2$—$R_3$—$NH_2$) to introduce the appropriate $R_4$ group and the appropriate $R_2$ group in the molecule, followed by acylation to introduce the

group, in accordance with the following equations:

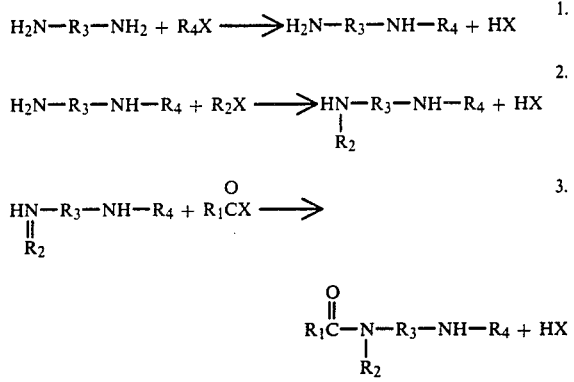

where X is a halide, such as bromine or chlorine.

The compound in which $R_4$ is dimethylpyrimidyl can be prepared by reacting the appropriate carbamimidoyl-substituted compound with 2,4-pentanedione in accordance with the following equation:

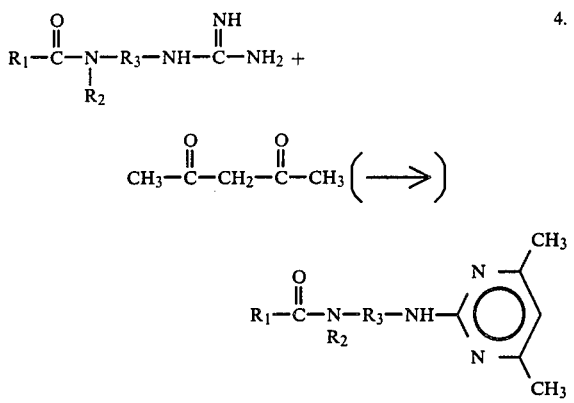

The steps given above for the preparation of the compounds of the invention need not be carried out in the order given, but can be carried out in any appropriate order, as will be apparent to those skilled in the art.

The reactants involved in the above reactions are all available or can be readily synthesized in a known manner. Similarly, appropriate conditions for carrying out the reactions will be obvious to those skilled in the art.

The following examples are presented to further illustrate the invention.

EXAMPLE I

1-N-carbamimidoyl-5-N-(2-octyl-cyclopropane-1-carbonyl)-pentamethylenediamine (A) 1-amino-5-guanidinopentane (I):

To 5 grams of 1,5-diaminopentane dissolved in 50 ml. of $H_2O$ was added dropwise a solution of 6 grams of S-methylthiopseudourea.$H_2SO_4$ dissolved in 100 ml. of $H_2O$. During the addition at room temperature and 15 hours thereafter, the reaction solution was stirred vigorously. During this period, $CH_3SH$ was evolved. After 15 hours, there was white precipitate, which was filtered; the filtrate was concentrated in vacuo to a viscous colorless oil, which upon the addition of 150 ml. of MeOH produced 2.8 g of white solid. The molecular weight was confirmed by mass spectometry.

(B) 2-(n-octyl)cyclopropanecarbonyl chloride (II)

2 grams of anhydrous $CuSO_4$ was suspended in 9 grams of 1-decene in a 2-neck round bottom flask. To one of the necks was fitted a water cooled condenser; to the other an addition funnel filled with a solution of 7.5 g. or ethyl diazoacetate dissolved in 10 grams of 1-decene. The $CuSO_4$ suspension was heated at 100° C. The dropwise addition of 1-decene solution of ethyldiazoacetate into the suspension was accompanied with nitrogen evolution. The reaction mixture was heated after the completion of addition until nitrogen evolution stopped. After filtering $CuSO_4$, the entire bulk of the reaction products was chromatographed quickly on silica gel, eluting with 1:1 mixture of low boiling petroleum ether and $CHCl_3$. The first fraction was the unreacted 1-decene, followed by 5.5 grams of a mixture of cis and trans ethyl 2-(n-octyl)cyclopropanecarboxylate. 4.0 grams of this mixture was hydrolyzed by refluxing with 2.4 g. of NaOH in 30 ml. of $H_2O$ for 10 hours. The hydrolysate was washed with ether to remove unreacted esters, then acidified to pH 1 with HCl, followed by extraction with ether. The concentrated ether extracts gave 2.2 g. of 2-(n-octyl)cyclopropanecarboxylic acid. The entire bulk of this acid was treated with excess amount of $SOCl_2$ at room temperature for 10 hours. Evaporation of excess $SOCl_2$ gave quantitative yield of products.

(C) 1-N-carbamimidoyl-5-N-(2-octyl-cyclopropane-1-carbonyl)pentamethylenediamine (III)

To 350 mg. of 1-amino-5-guanidinopentane suspended in 70 ml. of dry pyridine was added 700 mg. of the acid chloride (II). This mixture was stirred at room temperature for 2 days, after which the solid was filtered and the filtrate concentrated to a brown oil (1.19 g.). The entire bulk of this oil was chromatographed on silica gel, eluting with MeOH:$CHCl_3$ (2:3) and collecting 10 ml. fractions. Fractions 20–40 gave 28.8 mg. of desired product.

EXAMPLE 2

1-N-(4,6-dimethyl-2-pyrimidyl)-5-N-(2-octyl-cyclopropane-1-carbonyl)-pentamethylenediamine To 20 mg. of III dissolved in 1 ml. of ethanol in a vial was added 200 ml. of acetylacetone and 300 ml. of 70% aqueous $NaHCO_3$. The mixture was heated at 80° C. for 10 hours, then the products were basified to pH 13 and extracted with $CHCl_3$. The $CHCl_3$ extracts after drying over $MgSO_4$ gave 15 mg of product.

EXAMPLE 3

1-(2-n-octylcyclopropanecarboxamido)-4-guanidinobutane (A) 4-guanidino-1-butanamine (IV)

To 1.8 g. of 1,4-diaminobutane dissolved in 50 ml. of $H_2O$ was added, dropwise, a solution of 2 g. of S-methylthiopseudourea.$H_2SO_4$ in 20 ml. of $H_2O$. Throughout the addition, the solution was stirred vigorously and continued for 12 hours after the completion of addition. Then $H_2O$ was lyophilized, giving viscous colorless oil, which upon addition of 50 ml. of methanol precipitated 1.05 g. of white powder. Mass spec. (FD.) ions at m/e 228 and 130 for $H_2N—(CH_2)_4—NHC(=NH)—NH_2.H_2O_4$ and $H_2N—(CH_2)_4—NHC(=NH)—NH_2$, respectively.

(B) 1-(2-n-octylcyclopropanecarboxamido)-4-guanidinobutane (V)

To 457.2 mg. of 1-amino-4-guanidinobutane (IV) suspended in 60 ml. of dry pyridine was added 2-(n-octyl)cyclopropanecarbonyl chloride. This suspension was stirred at room temperature for 40 hours. At the end of 40 hours the solid material was filtered and the filtrate concentrated to a viscous oil, which was chromatographed on silica gel using 30% methanol in $CHCl_3$, resulting in 497.7 mg. of desired material, characterised by EIMS with M+ at m/e 310 for $C_{17}H_{34}N_4O$.

EXAMPLE 4

1-(2-n-octylcyclopropanecarboxamido)-4-(4,6-dimethyl-2-pyrimidylamino)-butane (VI)

To 20 mg. of V dissolved in 1 ml. of ethanol was added 200 ml of 2,4-pentanedione and 500 ml. of 10% aqueous $NaHCO_3$. The mixture was heated at 80° C. for 20 hours, then the products were basified to pH 13 with NaOH, and extracted with $CHCl_3$. The combined $CHCl_3$ extracts after concentration gave about 10 mg. of product, which compound was characterized by GC/MS, molecular ion at m/e 374 for $C_{22}H_{38}N_4O$.

EXAMPLE 5

1-(2-n-octylcyclopropanecarboxamido)-5-guanidinopentane (A) 5-guanidino-1-pentamine (VII)

To 5 grams of 1,5-diaminopentane dissolved in 50 ml. of $H_2O$ was added dropwise a solution of 6 grams of S-methylthiopseudourea.$H_2SO_4$ dropwise in 100 ml. of $H_2O$. During the addition at room temperature, the reaction solution was stirred vigorously, and was continued for 15 hours after the completion of the addition. During this period $CH_3SH$ was evolved. After 15 hours, there was some white precipitate, which was filtered; the filtrate was concentrated in vacuo to a viscous colorless oil, which upon the addition of 150 ml. of methane produced 2.8 g. of white solid. Elemental analysis. Calculated for $C_6H_{16}N_4.H_2SO_4$: C, 29.8; H, 7.05; n, 25.6; S, 13.3. Found: C, 28.87; H, 7.47; N, 24.16; S, 12.14. Mass spectrometry (FD): M+H at m/e 145 for $H_2N—(CH_2)_5NHC(=NH)NH_2$.

(B) 1-(2-n-octylcyclopropanecarboxamido)-5-guanidinopentane (VIII):

To 350 mg. of 1-amino-5-guanidinopentane suspended in 70 ml. of dry pyridine was added 700 mg. of 2-(n-octyl)cyclopropanecarbonyl chloride. This mixture was stirred at room temperature for 2 days, after which the solid was filtered and the filtrate concentrated to a brown oil (1.19 g.). The entire bulk of this oil was chromatographed on silica gel eluting with $MeOH:CHCl_3$ (2:3) and collecting 10 ml. fractions. Fractions 20-40 gave 28.8 mg. of desired products. Mass spectrometry (EI): M+ m/e 324 for $C_{18}H_{36}N_4O$.

EXAMPLE 6

1-(2-n-octylcyclopropanecarboxamido)-5-(4,6-dimethyl-2-pyrimidylamino)-pentane (IX)

To 20 mg. of VIII dissolved in 1 ml. of EtOH in a vial, was added 200 μl. of acetylacetone and 500 ml. of 70% aqueous $NaHCO_3$. The mixture was heated at 80° C. for 10 hours, then the products basified to pH 13 and extracted with $CHCl_3$. The $CHCl_3$ extracts after drying over $MgSO_4$ gave 15 mg. of products. Compound IX was characterized by GC/MS, molecular ion at m/e 338 for $C_{23}H_{40}N_4O$.

EXAMPLE 7

1-(2-n-octylcyclopropanecarboxamido)-6-guanidinohexane (A) 6-guanidino-1-hexanamine (X)

To 2.3 g. of 1,6-diaminohexane dissolved in 50 ml. of $H_2O$ was added dropwise with vigorous stirring a solution of 2 g. of S-methylthiopseudourea.$H_2SO_4$ in 20 ml. of $H_2O$. After the completion of addition, the stirring was continued for 15 hours, after which the precipitate (the diadduct) was filtered. The filtrate was concentrated to a viscous oil which upon the addition of 50 ml. of MeOH precipitated 718 mg. of white powder.

Elemental analysis. Calculated for $C_{17}H_{18}N_4.H_2So_4$: C, 32.81; H, 7.81; N, 21.88; S, 12.50. Found: C, 33.41; H, 8.32; N, 23.01; S, 11.89

(B) 1-(2-n-octylcyclopropanecarboxamido)-6-guanidinohexane (XI)

528 mg. of X was suspended in 50 ml. of dry pyridine, to which was added 477 mg. of 2-(n-octyl)cyclopropanecarbonyl chloride. The mixture was allowed to stir at room temperature for 3 days, after which the solid was filtered and the filtrate was concentrated to a brown oil, which was chromatographed on silica gel, eluting with 20% MeOH in $CHCl_3$, giving 106.3 mg. of the desired material. Mass spectrometry (EI): M+ at m/e 338 for $C_{19}H_{38}N_4O$.

EXAMPLE 8

1-(2-n-octylcyclopropanecarboxamido)-6-(4,6-dimethyl-2-pyrimidylamino)hexane (XII)

To 20 mg. of XI dissolved in 1 ml. of EtOH was added 200 ml. of 2,4-pentanedione and 500 ml. of 10% aqueous $NaHCO_3$. The mixture was heated at 80° C. for 15 hours, then the products were basified to pH 13 with NaOH and extracted with $CHCl_3$ extracts, which after drying over $MgSO_4$ gave about 10 mg of the desired products. Compound XII was characterized by GC/MS with molecular ion at m/e 402 for $C_{24}H_{42}N_4O$.

EXAMPLE 9

1-(2-n-octylcyclopropanecarboxamido)-5-(4,6-dimethyl-2-pyrimidylamino)pentane

To 1 g. of 1,5-diaminopentane dissolved in 10 ml. of $H_2O$ and heated to 40° was added slowly a solution of 0.75 g. of S-methylthiopseudourea.$H_2SO_4$ in 10 ml. of $H_2O$. After the completion of the addition the solution was stirred at 40° C. for 10 hours, and then concentrated to a syrupy oil. This oil was derivatized by adding 10 ml. each of 2,4-pentanedione, EtOH and 10% aqueous $NaHCO_3$, heated at reflux for 4 hours. The resultant solution was basified to pH 12 then extracted with $CHCl_3$. Evaporation of $CHCl_3$ gave a reddish brown liquid. 340 mg. of this liquid dissolved in 2 ml. of $Et_3N$, to which was added 100 mg. of the acid chloride in 3 ml. of $Et_3N$. The solution was stirred at room temperature for 45 minutes. GC/MS analysis: m/e at 388 for $C_{23}H_{40}N_4O$.

EXAMPLE 10

1-{N-[3-(3-methylbutanamido)propyl]-tetradecanamido}-5-(4,6-dimethyl-2-pyrimidylamino)pentane (A) 5-(4,6-dimethyl-2-pyrimidylamino)-1-pentanamine (XII)

To 1,5-pentanediamine (1 g) dissolved in 10 ml water was added S-methylthiopseudourea sulfate (1.36 g) in 10 ml. of water. The amine solution was held at 45°–48° during the addition which took 1 hour. Stirring was continued for 8 hours. The volume was evaporated to about 10 ml under a stream of N₂ on the steam bath. Ethanol (10 ml) and 10% NaHCO₃ (10 ml) plus 10 ml of 2,4-pentanedione were added and the solution refluxed overnight. After brief cooling the solution was acidified to pH 1–2 and heated at 90° for 10 min. The cooled acidified mixture was then extracted thoroughly with ether, basified with 2N NaOH, and extracted with CHCl₃. The combined CHCl₃ extracts were evaporated to yield the crude product which was used without purification, wt 996 mg.

(B) 1-(2-cyanoethylamino)-5-(4,6-dimethyl-2-pyrimidylamino)pentane (XIII)

To a stirred solution of (XII) (966 mg) in t-butanol was added 250 mg of acrylonitrile dissolved in 1 ml t-butanol over a period of 1 hour. Continued stirring for 3.5 hours at room temperature and finally refluxed for 1.5 hours. Chloroform was added and the product was extracted into 1N H₂SO₄. The aqueous phase was washed once with CHCl₃, then basified to pH 10 with 2N NaOH and the free amine extracted into CHCl₃. The product (XIII) 1.04 g was obtained by evaporation of the solvents under vacuum.

(C) 1-[N-(2-cyanoethyl)tetradecanamido]-5-(4,6-dimethyl-2-pyrimidylamino)-pentane (XIV)

Crude XIII was dissolved in dry pyridine to which 1 eq of tetradecanoyl chloride was added with stirring. The run was followed by tlc and excess acid chloride was added to drive the reaction to completion. Ice was then added to quench the reaction followed by the addition of CHCl₃. The mixture was first extracted with 10% NaHCO₃ and then with 1M HOAc to remove the bulk of the pyridine. The remaining CHCl₃ phase was evaporated to yield the crude product which was purified by chromatography on a 100 g silica gel (Brinkman 50–200μ) column developed with 30% acetone/chloroform. The product (1 g) was collected after only 150 ml of eluant had passed through the column and was only partially purified.

(D) 1-[N-(3-aminopropyl)tetradecanamido]-5-(4,6-dimethyl-2-pyrimidylamino)pentane (XV)

The nitrile (XIV) (330 mg) was dissolved in 5 ml of 10% conc. NH₃ in ethanol to which was added a spatula tip full of 5% Rh on alumina. After 5 hours stirring under 1 atm H₂, there was no reaction indicated by tlc or H₂ uptake. Additional catalyst (about 2×) and solvent were added and the hydrogenation continued overnight. The catalyst was filtered off and the solvents removed under vacuum to yield the product XV.

(E) 1-{N-[3-(3-methylbutanamido)propyl]-tetradecanamido}-5-(4,6-dimethyl-2-pyrimidylamino)pentane The primary amine XV was treated with 3-methylbutanoyl chloride in pyridine in the manner described above (C). The crude product was chromatographed on a 24 g silica gel column (BioSil A) of dimensions 1 cm (id)×30 cm, developed with 30% acetone/CHCl₃. Five ml fractions were collected. The pure product was found in tubes 14–22, 128 mg.

The compounds of the invention are useful in that they possess bactericidal properties against a wide variety of bacteria, including *S. pyogenes, B. subtilis, S. aureus, K. pneumoniae, M. avium, B. fragilis, C. perfringens,* and *C. albicans.*

The foregoing detailed description has been given for clearness of understanding only, and no unnecessary limitations should be understood therefrom as modifications will be obvious to those skilled in the art.

What is claimed is:

1. A synthetically produced substantially pure compound having the formula

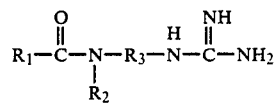

wherein $R_1$ is alkyl having 1–20 carbon atoms; cycloalkyl having 3–20 carbon atoms; alkylcycloalkyl or cycloalkylalkyl having 4–20 carbon atoms; phenyl; or phenyl substituted with a C1–C20 alkyl group;

$R_2$ is hydrogen or $C_1$–$C_{10}$ alkyl; and $R_3$ is a cyclic, straight or branched chain hydrocarbon group having 2–12 carbon atoms.

2. A compound in accordance with claim 1 wherein $R_1$ has 11–17 carbon atoms, and $R_3$ is a straight chain —$(CH_2)_n$, where n is an integer from 2 to 12.

3. A compound in accordance with claim 2 wherein $R_2$ is hydrogen.

4. A compound in accordance with claim 1 selected from 1-(tetradecanamidomethyl)-4-(guanidinomethyl)cyclohexane 1-benzamido-5-guanidinopentane 1-(5-phenylpentanamido)-5-guanidinopentane 1-(N-methyltetradecanamido)-5-guanidinopentane 1-[N-(7-methyloctyl)-tetradecanamido]-5-guanidinopentane 1-N-carbamimidoyl-5-N-(2-octyl-cyclopropane-1-carbonyl)-pentamethylenediamine 1-(2-n-octylcyclopropanecarboxamido)-4-guanidinobutane 1-(2-n-octylcyclopropanecarboxamido)-5-guanidinopentane 1-(2-n-octylcyclopropanecarboxamido)-6-guanidinohexane.

* * * * *